(12) United States Patent
Reinhardt et al.

(10) Patent No.: US 6,655,213 B1
(45) Date of Patent: Dec. 2, 2003

(54) METHOD FOR EXAMINING A SOLIDIFIED AND/OR HARDENING MATERIAL USING ULTRASOUND, RECEPTACLE AND ULTRASOUND SENSOR FOR CARRYING OUT THE METHOD

(75) Inventors: H. W. Reinhardt, Stuttgart (DE); Christian W. Grosse, Stuttgart (DE); Alexander Herb, Stuttgart (DE); Bernd Weiler, Urbach (DE); Günther Schmidt, Tübingen (DE)

(73) Assignee: Universitat Stuttgart (DE)

( * ) Notice: Subject to any disclaimer, the term of this patent is extended or adjusted under 35 U.S.C. 154(b) by 0 days.

(21) Appl. No.: 09/857,536

(22) PCT Filed: Nov. 27, 1999

(86) PCT No.: PCT/DE99/03760

§ 371 (c)(1),
(2), (4) Date: Sep. 10, 2001

(87) PCT Pub. No.: WO00/34769

PCT Pub. Date: Jun. 15, 2000

(30) Foreign Application Priority Data

Dec. 7, 1998 (DE) .......................................... 198 56 259

(51) Int. Cl.$^7$ ............................................. G01N 29/08
(52) U.S. Cl. ............................... 73/597; 73/600; 73/602
(58) Field of Search .......................... 73/597, 598, 599, 73/600, 602, 594

(56) References Cited

U.S. PATENT DOCUMENTS

| | | | | |
|---|---|---|---|---|
| 4,259,868 A | * | 4/1981 | Rao et al. | 73/597 |
| 4,377,087 A | * | 3/1983 | Rodot | 73/594 |
| 4,380,930 A | * | 4/1983 | Podhrasky et al. | 367/13 |

(List continued on next page.)

FOREIGN PATENT DOCUMENTS

| | | |
|---|---|---|
| DE | 26 17 779 A1 | 11/1977 |
| DE | 196 29 485 A1 | 1/1998 |
| JP | 07020097 A | 1/1995 |
| WO | WO99/04254 A1 | 1/1999 |

OTHER PUBLICATIONS

U. Grosse, W. Reinhardt: Continuous Ultrasound Measurement During Setting And Hardening of Concrete in Otto Graf–Journal, vol. 5, 1994, Side 76—98.

N. Mikhailov, Chr. U. Grosse "An Automatic Picker of the Onset Time of Acoustic Emission Signals", Otto Graf Journal, vol. 6, 1995, S. 168, 169, 174—179.

*Primary Examiner*—Hezron Williams
*Assistant Examiner*—Rose M. Miller
(74) *Attorney, Agent, or Firm*—George W. Neuner; Edwards & Angell, LLP

(57) ABSTRACT

A method is described for examining a solidifying and/or hardening material such as cement, concrete or the like, using ultrasound waves emitted by an ultrasound transmitter, which penetrate the solidifying and/or hardening material, are continuously measured and analyzed. During solidification and/or hardening of the material, the signal shapes of the ultrasound waves penetrating the material, are recorded. The change with time of the compression wave velocity and/or the relative energy of the ultrasound waves and/or the frequency spectra of the ultrasound waves is extracted from the ultrasound wave shapes during the entire course of solidification and/or hardening of the material. This change with time of the compression wave velocity and/or the relative energy of the ultrasound waves and/or the frequency spectra of the ultrasound waves is approximated through a compensating function, preferably the Boltzmann function. The free parameters of the compensation function are associated with material properties and permit comparison of a current measurement with reference values of these parameters to permit determination of material properties of the examined material. A receptacle and an ultrasound transmitter for carrying out the method also are described.

4 Claims, 9 Drawing Sheets

U.S. PATENT DOCUMENTS 4,754,645 A * 7/1988 Piche et al. .................... 73/597
5,178,005 A * 1/1993 Peterson .................. 73/152.11
5,265,461 A * 11/1993 Steiger et al. ................. 73/38
5,741,971 A * 4/1998 Lacy ....................... 73/152.16
5,992,223 A * 11/1999 Sabins et al. ............... 73/54.03
6,112,599 A * 9/2000 Maki, Jr. ..................... 73/587

* cited by examiner

METHOD FOR EXAMINING A SOLIDIFIED AND/OR HARDENING MATERIAL USING ULTRASOUND, RECEPTACLE AND ULTRASOUND SENSOR FOR CARRYING OUT THE METHOD

BACKGROUND OF THE INVENTION

The invention concerns the examination of a solidifying and/or hardening material, such as cement, concrete or the like, using ultrasound waves, emitted from an ultrasound transmitter to an ultrasound receiver, which penetrate the material and are continuously measured and analyzed.

PRIOR ART

Such examinations are known e.g. from the publication "Kontinuierliche Ultraschallmessungen während des Erstarrens and Aushärtens von Beton" (continuous ultrasound measurements during solidification and hardening of concrete) by Chr. U. Grosse and H.-W-Reinhardt in Otto-Graf-Journal, Vol. 5, 1994.

Ultrasound waves can penetrate a material without causing damage thereby being influenced by the elastic properties of the material, which produces information about the elastic properties.

With concrete, these are e.g. its current solidification and hardening state, composition (grading curve, water-cement value etc.) and the entrained air content and possibly utilized additional means.

In industrial construction e.g., determination of solidification start and end of cement paste according to DIN EN 196, part 3, is carried out through the Vicat method. A measurement of this type is not possible with concrete due to the aggregate and is therefore not provided in the above-mentioned standard. Examination methods for unset concrete have been, on the one hand, consistency measuring methods such as the propagation test and compacting test according to DIN 1048 part 1, the penetrometer according to ASTM C-403 and the setting test according to DIN ISO 4109. On the other hand, there is the air content measurement according to DIN 1048 part 1 including pressure compensation method and furthermore methods for determining the water content.

The latter methods permit only individual measurements at fixed points in time and give information about a certain property. It is not possible to obtain detailed information about the composition of the material nor about the further hardening of the material after solidification.

OBJECT OF THE INVENTION

It is therefore the underlying purpose of the invention to provide reliable use of an ultrasound test method in industrial practice and permit easy continuous monitoring of the state of a solidifying and/or hardening material.

SUBJECT MATTER AND ADVANTAGES OF THE INVENTION

This object is achieved by a method for examining a solidifying and/or hardening material such as cement, concrete or the like, using ultrasound waves emitted by an ultrasound transmitter, which penetrate the solidifying and/ or hardening material, are continuously measured and analyzed, comprising the following method steps:

i) during solidification and/or hardening of the material, the signal shapes of the ultrasound waves penetrating the material are recorded;

ii) The change with time of the compression wave velocity and/or the relative energy of the ultrasound waves and/or the frequency spectra of the ultrasound waves is extracted from the ultrasound wave shapes during the entire course of solidification and/or hardening of the material.

iii) This change with time of the compression wave velocity and/or the relative energy o the ultrasound waves and/or the frequency spectra of the ultrasound waves is approximated through a compensating function, preferably the Boltzmann function.

iv) the free parameters of the compensation function are associated with material properties.

v) the free parameters of the compensation function permit comparison of a current measurement with reference values of these parameters to permit determination of material properties of the examined material.

Automatic measuring and analysis of the data is largely possible and information about the material itself can be obtained already during the solidifying/hardening phase.

For the measurement, the material to be examined is introduced into a receptacle and compacted. The opposing sides of the receptacle are provided with a preferably broadband (i.e. adequately linear frequency response function over a broad spectral range) ultra sound transmitter and a corresponding receiver. Same transforms the acceleration signal into a voltage signal and transmits it to a computer-controlled analog-digital transformer card which stores the signal in digital form thereby making it accessible for further analysis.

For an analysis, the velocity of the compression wave $v_p(T)$, the relative energy $E(T)$ of a measured signal, and the frequency spectrum $f(T)$ of the signal can be extracted with corresponding algorithms. The velocity of the compression wave $v_p(T)$, the relative energy $E(T)$ of a measured signal and the frequency spectrum $f(T)$ of the signal depend on the time T elapsed since production of the material and form together a complete parameter set which contains the entire information about the material which can be obtained from elastic waves.

The wave velocity of the compression waves in the material can be determined from the quotient between running distance s and running time $t(T)$ of the waves according to $v_p(T) = s/(t(T) - t_0)$. While the running distance s, determined through the dimensions of the receptacle, is constant, the running time $t(T)$ of the signals is reduced with increasing solidification of the material during the duration T of the test. In this calculation, constant parts for the running time of the waves through the walls of the container and for the time delay, caused by the measuring means, must be subtracted from the determined running time. This dead time $t_0$ of the system which is not related to the material can be determined through calibration measurement, which can be achieved in the most simple fashion through running time measurement with direct coupling of transmitter and receiver container walls.

The relative energy $E(T)$ is defined as a quotient of the wave energy which can be measured after passage of the wave through the material, and the energy which was introduced into the material by the ultrasound pulse. The individual energies are thereby calculated from the integral of the amplitude squares of the respective signals. If the introduced energy cannot be used as measuring value, it can be assumed to be constant when using a suitable ultrasound transmitter. The relative energy increases with increasing hardening or solidification of the material. The energy can further be represented as its integral overtime.

If the utilized ultrasound transmitter can generate sufficiently short impulses, the transmitted ultrasound wave contains more than one certain frequency. A broad continuous frequency spectrum up to a certain limit frequency is excited which is reciprocal to the impulse duration. Depending on the hardening or solidifying state, the material can transmit different frequency portions in a different manner. After the measurement, the spectrum of the signals can be calculated through Fourier transformation. If these individual spectra are normalized to their maximum, added chronologically and the spectral amplitudes are graphically represented as grey values, one obtains so-called contour plots. This three-dimensional representation permits calculation of frequency time curves or frequency time areas per individual measurement e.g. through calculation of average frequency maxima. These representations permit tracking of the spectral transition properties of the material as a function of time.

Correlation with previous measurements or with existing reference curves for velocity and energy produces e.g. findings concerning the composition of the material.

The measured curve shapes are examined more closely with respect to use of ultrasound technology within quality control with the aim of modelling the variation of the measured values (velocity, energy, frequency) with time in dependence on the material composition and nature. This is thus the solution of an inversion problem with unknown material properties. The inventive method facilitates classification of the material within quality control after adjustment to the respective task.

To achieve this object, functions with sufficient free parameters must be used by means of which the curve shapes which are typical for the change of the measured variable vp, E and f can be interpreted. The Boltzmann function which is known from thermodynamics is e.g. particularly suited for the velocity:

$$y(x) = \frac{A_1 - A_2}{1 + e^{\frac{x - x_0}{dx}}} + A_2$$

It contains the four free parameters $A_1$, $A_2$, $x_0$ and dx whose values can be used for adjusting the compensating function to the measuring curves. The quality of the inversion curves calculated e.g. for the velocity is more than sufficient for the practical application of the method. All four free parameters can be used for a detailed classification of the materials. The parameter $A_2$ e.g. can be associated with the water/cement value W/Z when examining unset concrete.

In a further development of the inventive method, an other embodiment is characterized in that the arrival time of an ultrasound wave (initial use) is determined automatically with an algorithm which is based on the sum of the partial energy of the digitized received signal, wherein the energy course $S_i$ of the digitized signal is determined by the sum of the amplitude squares $x_k^2$:

$$S_i = \sum_{k=0}^{i} x_k^2$$

wherein $x_k$ is the $k^{th}$ sample point of the digitized signal and the minimum of the energy course $S_i$ is determined which results from correction of $S_i$ with a trend δ:

$$S_i' = \sum_{k=0}^{i} x_k^2 - i\delta$$

with $$\delta = \frac{S_N}{\alpha \cdot N},$$

wherein $S_N$ is the partial energy at the last sample point N and α is iteratively determined through comparison of the corrected energy course $S_i'$ with the measured wave shape of a received ultrasound signal, and the arrival time of the ultrasound wave (initial use) is associated with the minimum of the corrected energy course $S_i'$.

In this embodiment, the arrival time of the ultrasound signal at the receiver is determined thereby producing the running time. To determine this so-called initial use, an algorithm has been developed which is based on the partial energy and the use of the Hinkley criterion, which permits a robust and very simple approach for initial use detection. The sum of the partial energy $S_i$, of an individual digitized wave signal can be represented as sum of the amplitude squares $x_k^2$ as below:

$$S_i = \sum_{k=0}^{i} x_k^2$$

The sample point i thereby corresponds to a certain time during the signal. Arrival of the signal is thereby characterized by a significant rise of this energy sum. With respect to the algorithm, this means that the minimum of the sum curve must be automatically recognized from partial energy minus a negative trend 8 suitably selected according to the signal noise:

$$S_i' = \sum_{k=0}^{i} x_k^2 - i\delta$$

The trend may be represented e.g. as follows;

$$\delta = \frac{S_N}{\alpha \cdot N}$$

$S_N$ is the energy at the last sample point N. An automatic iteration routine was implemented for the variable a value for adjustment to the signal quality.

The inventive method can be carried out in industrial practice for reliable and easy continuous monitoring of the state of a solidifying and/or hardening material by means of an inventive receptacle and an inventive ultrasound transmitter. The receptacle preferably comprises a U-shaped part (24) from a highly-dampening material and two rigid container walls (22,23), from a material which permits emitting plane waves, for mounting an ultrasound transmitter (3) and an ultrasound receiver (4), wherein the shaped part (24) and the container walls (22,23) delimit a receiving space for the material to be examined, characterized in that the U-shaped part (24) is pressed by means of connecting elements (25) engaging on the two container walls (22,23), between the two opposite container walls (22,23). The ultrasound transmitter preferably comprises means for generating the ultrasound pulses through acceleration of a sphere (8) to exert an impulse, having a large frequency content, onto the wall of a receptacle, characterized in that the means for accelerating the sphere (8) are formed by a compressed gas acting directly onto the sphere (8) or through an electric lifting magnet moved towards the sphere (8).

The shaped part of the receptacle acoustically decouples the container walls thereby providing at the same time secure sealing of the receiving space to prevent leakage of the material from the receiving space. The construction by means of the connecting elements facilitates assembly and disassembly of the receptacle into its individual parts for cleaning.

The ultrasound transmitter comprises means for accelerating a sphere which are formed by compressed gas or a movable lifting magnet. This permits reproducible ultrasound generation with simple means.

Although the invention is described with respect to the hardening of concrete, the inventive method or parts thereof is/are not limited to the examination of concrete but also applicable for other materials, composite materials, plastic materials etc.

DESCRIPTION OF THE EMBODIMENT

Figure 1:
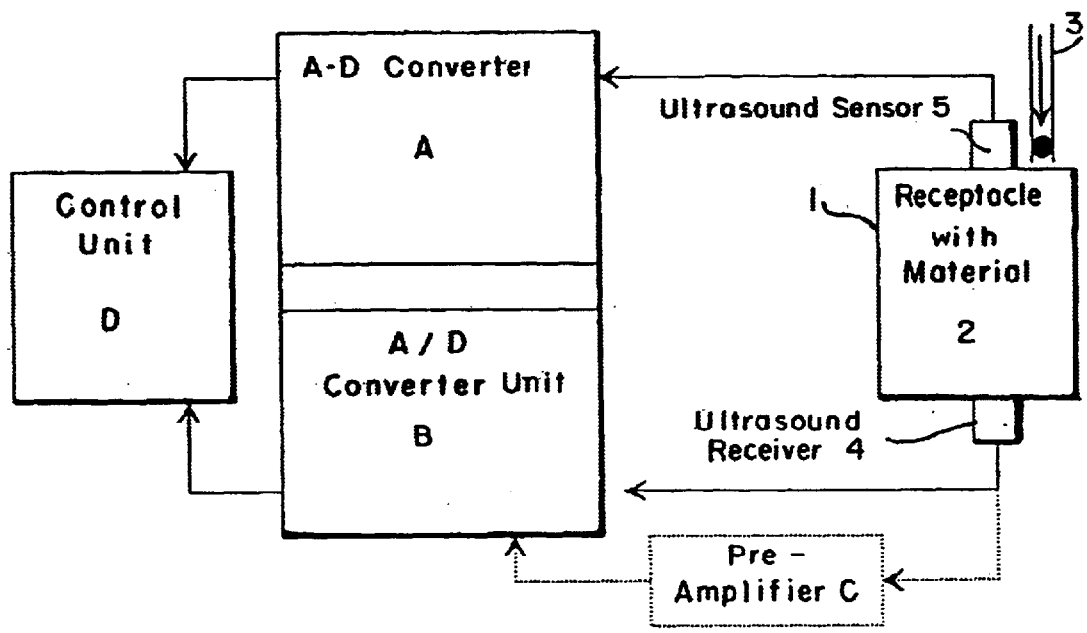
FIG. 1 shows a schematic diagram of the experimental arrangement for examination of a material using ultrasound.

The principle of the measurement is schematically shown in FIG. 1. A receptacle 1 contains a material 2 to be examined. An ultrasound transmitter or impactor 3 transmits an ultrasound pulse via the wall of the receptacle 1 into the material 2 to be examined. At the same time it triggers the A-D converter card A which starts the measurement. After a certain running time, the ultrasound waves arrive at the ultrasound receiver 4. The ultrasound receiver 4 converts the acceleration signal into the voltage values which are then digitized and stored by the A/D converter unit B. A preamplifier C is provided before the A/D converter unit B. The A/D converter units A and B are connected to an evaluation and control unit D. The changes with time of propagation velocity, energy and frequency of the ultrasound waves give information about the material properties. The ultrasound sensor 5 provided for checking is only required if an impactor is used as excitation.

Figure 2:
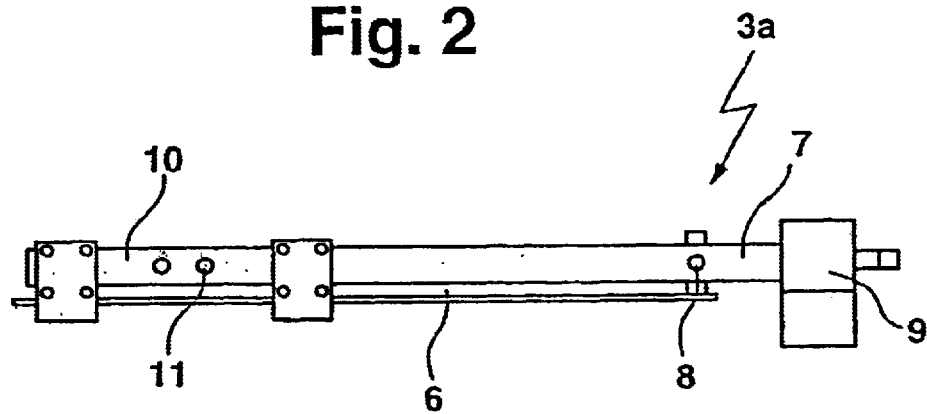
FIG. 2 shows a longitudinal section through an ultrasound transmitter for carrying out the method of FIG. 1.

The ultrasound transmitter 3a of FIG. 2 consists of a non-magnetic pipe 6 whose end 7 facing away from the receptacle holds a sphere 8 of ferritic steel through permanent magnets. This pipe end 7 is provided with an electrically actuated solenoid valve 9 which permits exertion of a compressed gas impact onto the sphere 8. This compressed gas impact removes the sphere 8 from the permanent magnet, the sphere is accelerated by the spreading gas in the direction of the pipe end 10 facing the receptacle and hits the housing wall of the receptacle, thereby spreading a short broad-band ultrasound pulse. Upon impingement, the sphere 8 loses only part of its energy and the remaining impulse returns it into its initial position where it is again held by the permanent magnet. The bores 11 prevent compression of the air column before the sphere 8 and thereby deceleration of the accelerated sphere 8. To determine the speed of the sphere 8, there is a light barrier directly in front of the opening of the steel pipe 6 via which the sphere 8 hits the housing wall. A safety means acting onto the solenoid valve prevents inadvertent triggering of the compressed gas impact. A viewing glass permits monitoring of the position of the sphere 8 in the initial position. $CO_2$ is preferably used as compressed gas by connecting a gas bottle to the solenoid valve 9. The gas pressure can be controlled and changed by means of a pressure adjustment means. The impulse energy can be varied either in this fashion or through changing the valve opening time. Selection of an individual compressed gas impact, delayed compressed gas impact or multiple compressed gas impact is possible by means of the control device via the solenoid valve. The trigger signal for the compressed gas impact can be triggered either manually or via TTL trigger signals. The delay time for the delayed compressed gas impact or time between two compressed gas impacts can be adjusted to between 1 s and several minutes.

Figure 3:
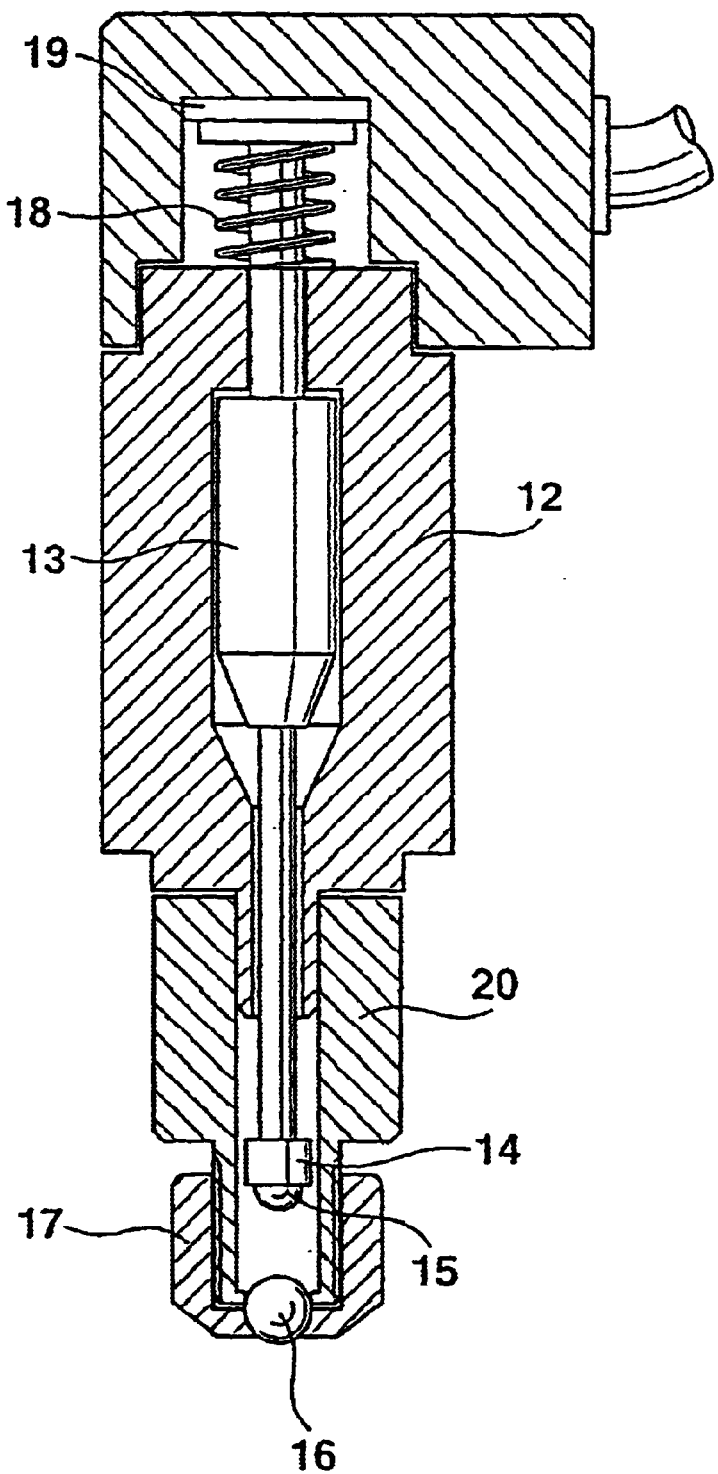
FIG. 3 shows a longitudinal section through another ultrasound transmitter for carrying out the method of FIG. 1.

FIG. 3 shows an ultrasound transmitter 3b comprising a lifting magnet having a coil form 12 and a displaceable armature 13. A spherical cap 15 is fixed to the armature tip 14. A voltage impulse from a control device supplies current to the coil form 12 such that the armature 13 is accelerated from its rest position. Just before the armature 13 reaches its maximum deflection, the spherical cap 15 meets the sphere 16 held by a fastening means (union nut) which transfers the impact as ultrasound pulse onto the receptacle. A restoring spring 18 returns the armature 13 into its rest position where it remains on a dampening seat plate 19 until the next voltage impulse. The sphere 16 can be replaced by means of the removable mounting means 17 to vary the contact time during impact and thereby the impulse width (frequency width). A connecting piece 20 is produced from electrically insulating material. The spherical cap 15 is connected to the armature in an electrically conducting fashion. A voltage applied between the sphere 16 and the armature 13 is short-circuited for the duration of the impact contact time. This produces a trigger impulse for external devices whose length corresponds to the contact time. To obtain different impulse strengths or energies, the length of the voltage impulse can be changed in the control device. For this purpose, lifting magnets of different powers can be used.

Figure 4:
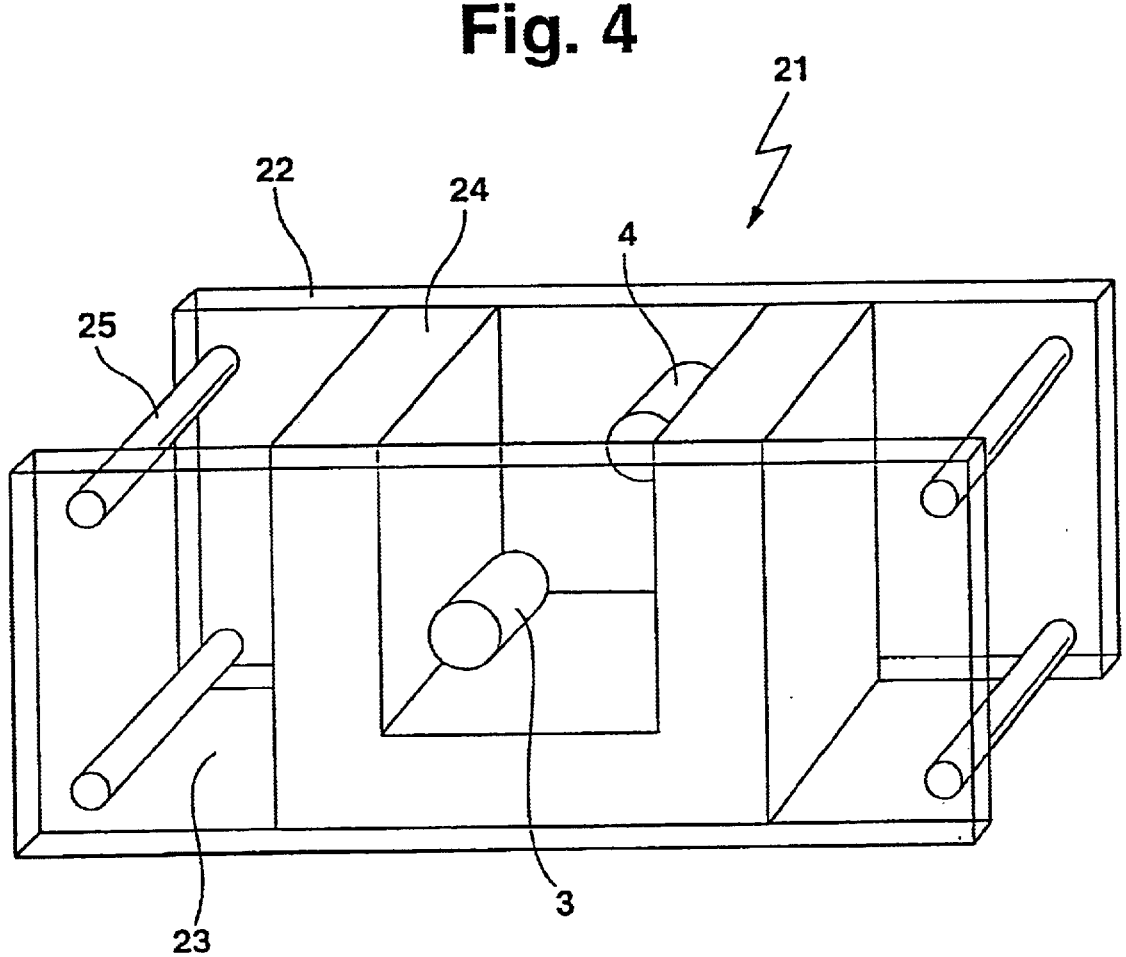
FIG. 4 shows a representation of a receptacle for carrying out the method of FIG. 1.

The receptacle 21 in accordance with FIG. 4 has 2 container walls 22, 23 from a rigid transparent material between which a U-shaped part 24 of elastic material (e.g. rubber) is disposed. The rigid container walls 22, 23 are interconnected via connecting elements 25 thereby fixing the elastic shaped part between them. An ultrasound transmitter 3 is disposed on the container wall 23 opposite to an ultrasound receiver 4 mounted to the container wall 22. The receptacle 21 can accommodate a hardening and/or solidifying material to permit ultrasound examination thereof in situ during hardening. The receptacle provides also contact between material and ultrasound transmitter 3 and receiver 4 via the container walls 22, 23. The container 21 has hardly any effect on the examination of the material since its acoustic properties are worse. Attenuation of the ultrasound waves in the container walls 22,23 and in the shaped part 24 is larger than in the material to be examined. The container is constructed from few parts which are easy to handle and clean and additionally can be re-used. Due to their rigid form, the container walls 22,23 produce radiation of almost plane waves, thereby omitting near-field effects. This permits on the one hand smaller container geometries (for point sources and propagation of spherical waves, measurements with a running distance smaller than double the wavelength would be problematic). On the other hand, the measurement accuracy is increased since deviations in the centered arrangement of ultrasound transmitter 3 and receiver 4 have only a negligible influence on the examinations. The shaped part 24 acoustically decouples the container walls 22,23 and meets the task of sealing. The connecting elements 25 of which only one has a reference numeral, connect the free ends of the container walls in an acoustically non-coupling, elastic and detachable fashion. The container walls 22,23 are pressed onto the shaped part 24. In addition, a rubber lid (not shown) can prevent evaporation of water which would falsify the measurement.

Figure 5:
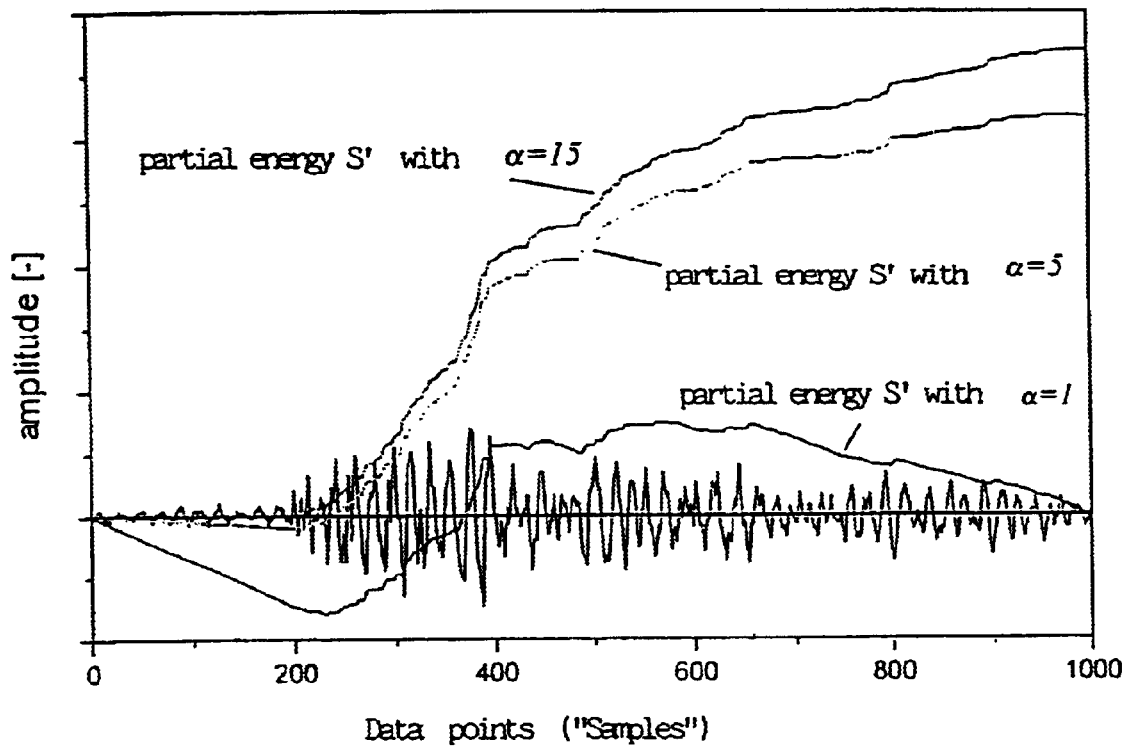
FIG. 5 shows a representation of the measured behavior of an ultrasound signal while carrying out the method of FIG. 1, and of the sum of the partial energy of the signal with 3 different values for the trend.

FIG. 5 shows the principle of automatic detection of the time of initial use for determining the compression wave velocity. The measured wave shape of an ultrasound signal is shown as an example. The sum of the partial energy of the signal is shown with 3 different values for the trend δ on the same time axis. One can derive therefrom that α=5 is most suited for determining the minimum energy, corresponding to the arrival times of the waves. The initial use for α=15 is selected too early, for α=1 too late. The algorithm used produces this optimum result.

Figure 6:
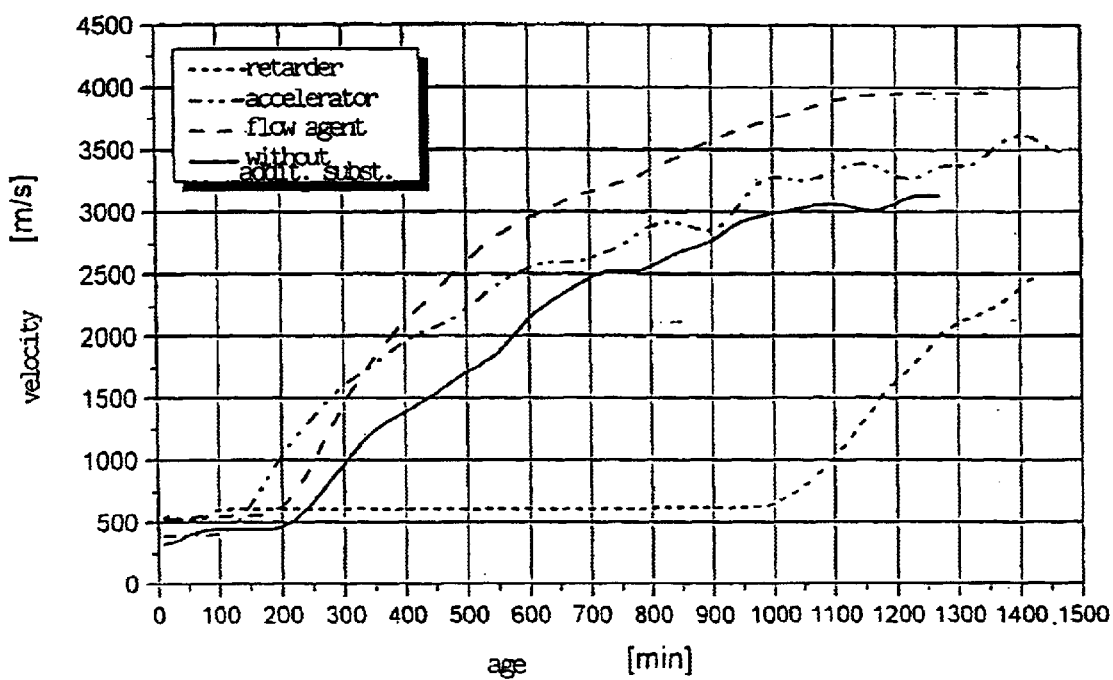
FIG. 6 shows a representation of the measured behavior of the change with time of the propagation velocity of ultrasound waves while carrying out the method of FIG. 1 on mortar having different additional substances.
Figure 7:
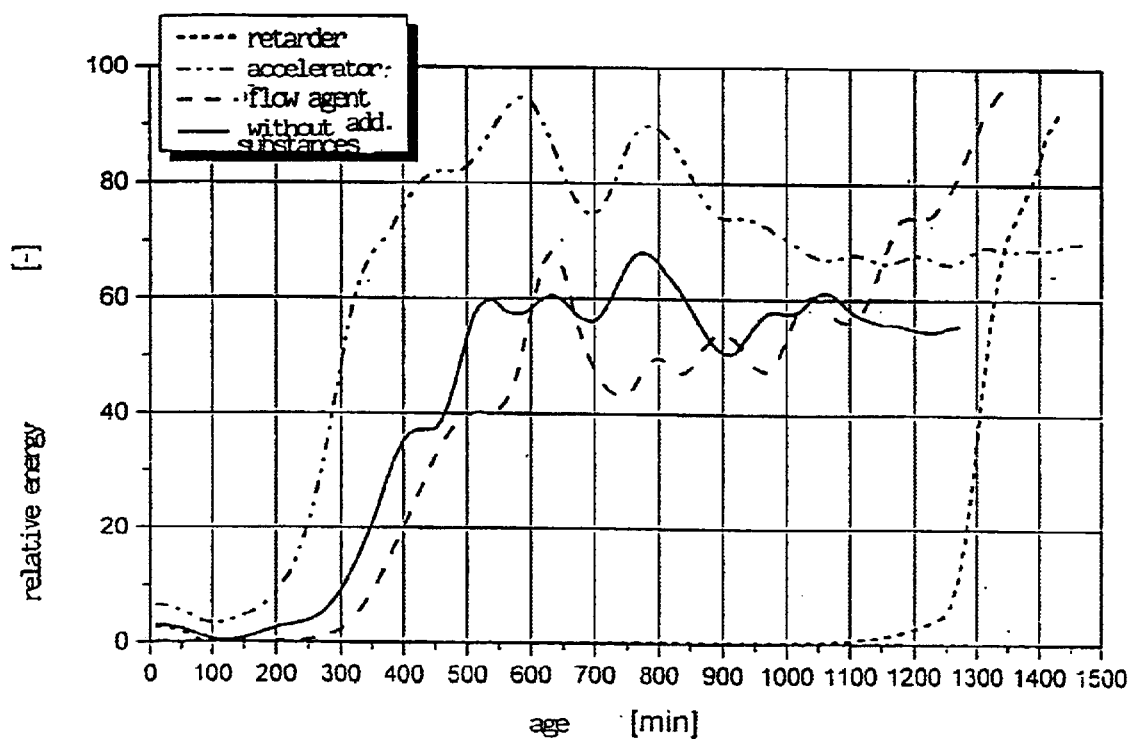
FIG. 7 shows a representation of the measured behavior of the change with time of ultrasound wave energy while carrying out the method of FIG. 1 on mortar having different additional substances.
Figure 8:
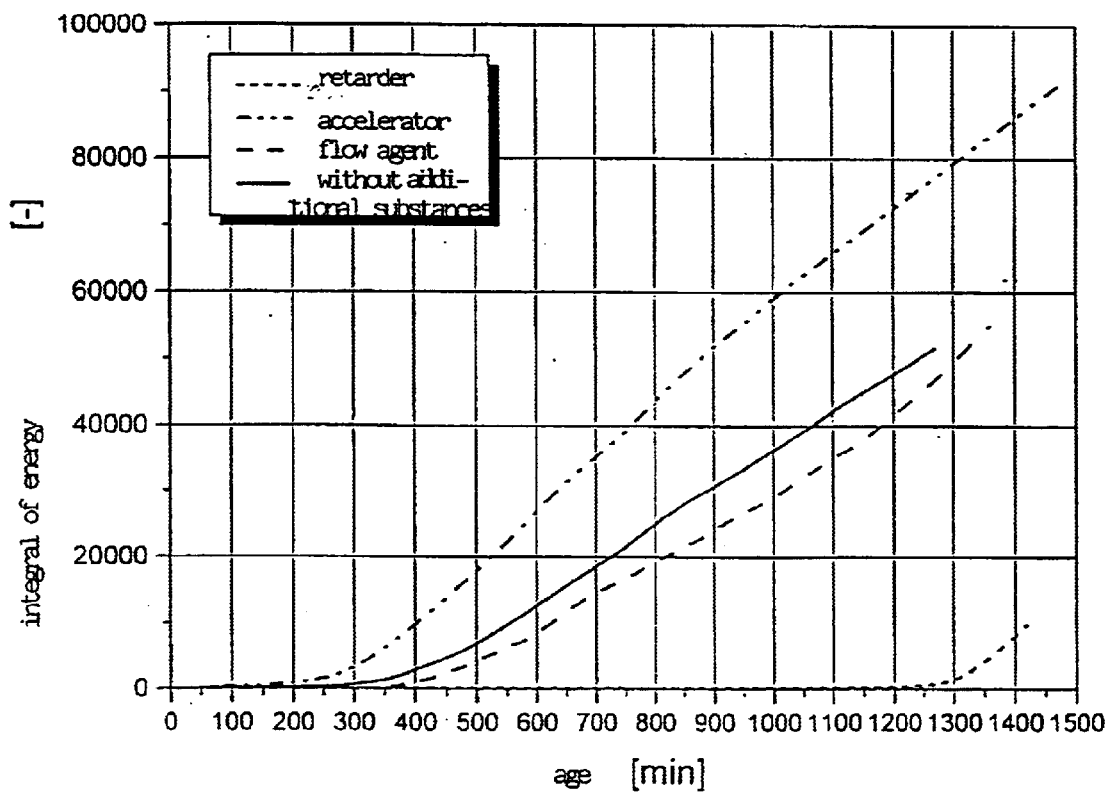
FIG. 8 shows a representation of the measured behavior of the change with time of the energy integral of ultrasound waves while carrying out the method of FIG. 1 on mortar having different additional substances.
Figure 9:
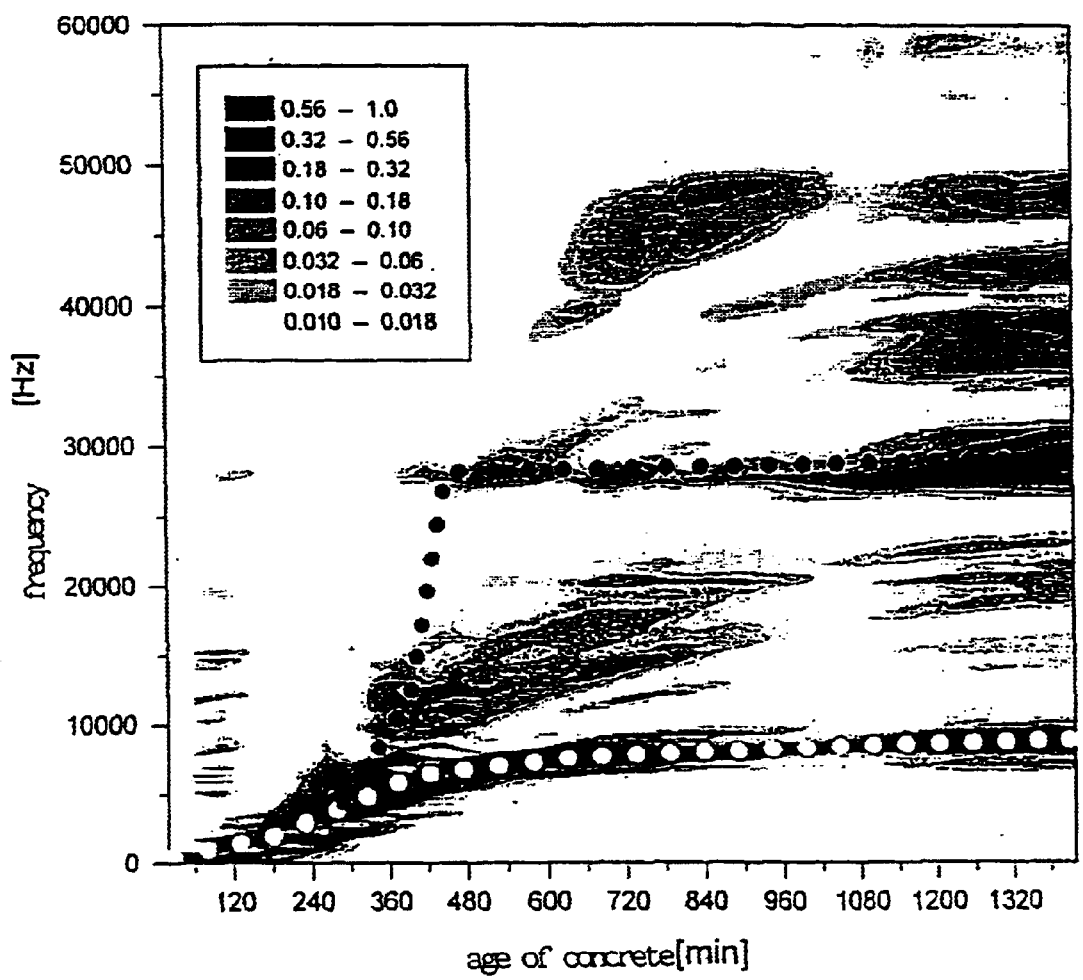
FIG. 9 shows a contour plot illustrating the measured behavior of the time changes of the frequency spectra while carrying out the method according to FIG. 1 on concrete, and also a frequency-time curve derived therefrom.

The following figures show exemplarily a representation of the change of the velocity of the compression wave $v_p(T)$, the relative energy E(T) of a measured ultrasound signal, and the frequency spectrum f(T) of the ultrasound signal as a function of time. FIG. 6 shows the change of the propagation velocity of the sound waves with the example of mortar without and with three different additional substances. The change of energy is analogously plotted against time in FIG. 7. Both figures show the rise of velocity or energy at different times corresponding to the different properties of the additional substances. The quantity of the rise and point in time when a certain final value of the velocity or energy has been reached also varies. A variant is shown in FIG. 8, i.e. an integral of the energy wherein the slope of the curves show great differences. The change of the frequency spectra is shown in FIG. 9 with respect to measurement of concrete. The spectra show large low-frequency portions at the start of the measurement and increasing broadening of the frequency band during further progress. The use of broad-band ultrasound sensors produces characteristic frequency-amplitude representations against time for different materials or materials with varying elastic properties. From the frequency-amplitude representation, curves can be derived, which are easier to analyze. Determination, e.g. by calculation of the frequency maxima in the region of 0–20 kHz produces the lower dotted curve of FIG. 9, which is typical for this material. Such a curve can be determined also for further frequency ranges (e.g. 20–60 kHz) (upper curve). The area between the curves describes characteristic material parameters.

Figure 10:
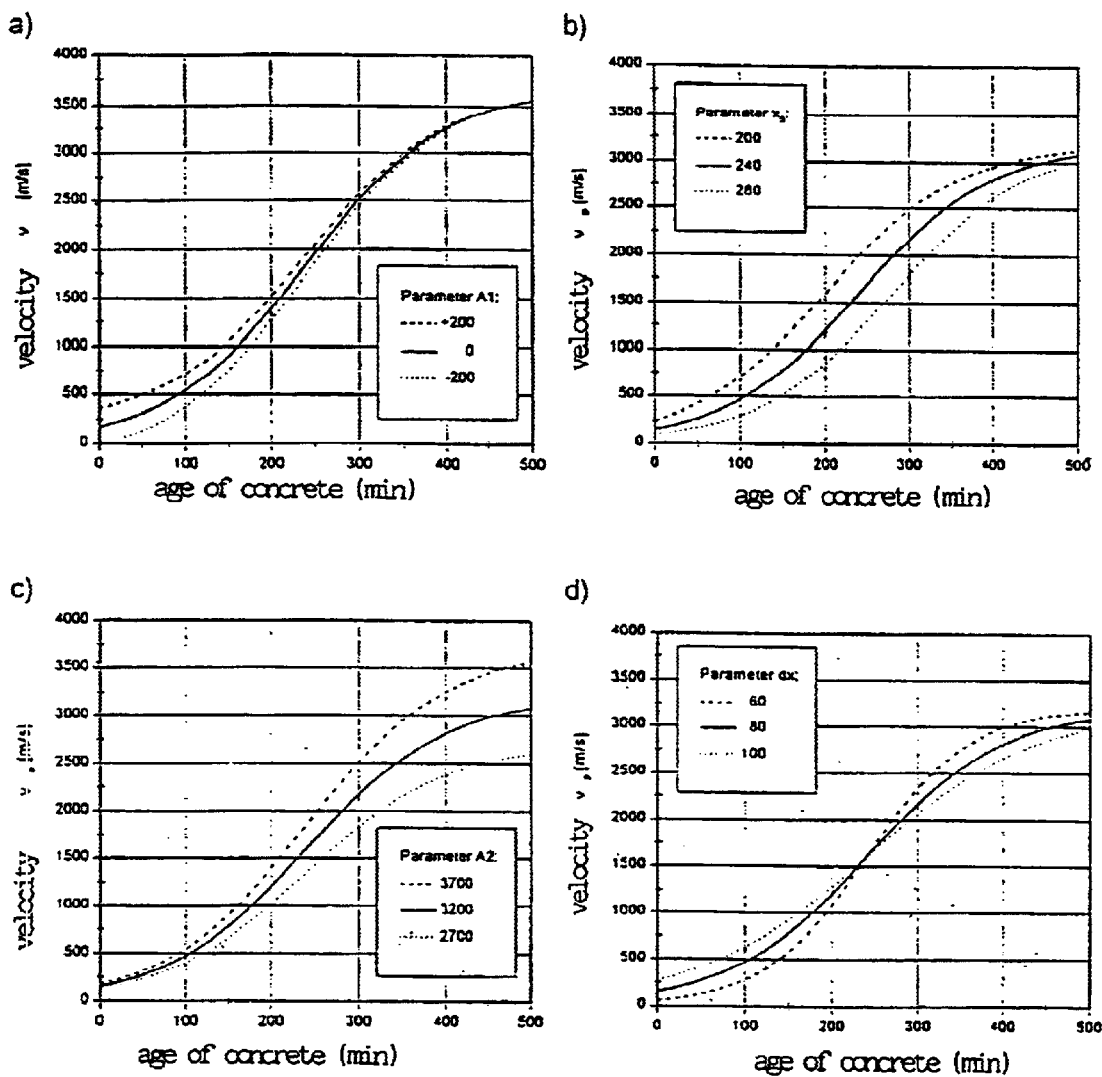
FIG. 10 shows a parameter study for adjusting a compensation function to the dependence of the change with time of the propagation velocity of ultrasound waves while carrying out the method of FIG. 1.

FIG. 10 shows a parameter study for adjusting the Boltzmann function selected as compensating function, to the behavior of the variation of the wave velocity in time. In this illustrated measurement with the described method, the material was concrete. Corresponding to their mathematical formulation $$y(x) = \frac{A_1 - A_2}{1 + e^{\frac{x-x_0}{dx}}} + A_2$$

the four free parameters $A_1$, $A_2$, $x_0$ and dx are varied. The free parameters are determined through optimum adjustment of the compensation function to the variation of the propagation velocity in time. Reference values of the free parameters are known from the reference measurements which correspond to certain material properties, such as rigidity, hardness, grain size or the like. When a material is to be examined, the current values of the free parameters are determined and compared with the reference values to obtain information about the properties of the examined material.

What is claimed is:

1. A method for examining a solidifying and/or hardening material such as cement, concrete, or the like, using ultrasound waves emitted by an ultrasound transmitter, wherein the ultrasonic waves penetrate the solidifying and/or hardening material and are continuously measured and analyzed, the method comprising the following method steps:

i) recording the signal shapes of the ultrasound waves penetrating the material during solidification and/or hardening of the material;
   ii) extracting from the ultrasound wave shapes during the entire course of solidification and/or hardening of the material at least one property selected from the group consisting of:
      a. the change with time of the compression wave velocity,
      b. the relative energy of the ultrasound waves, and
      c. the frequency spectra of the ultrasound waves;
   iii) approximating the property of step ii) by a compensating function having free parameters;
   iv) associating the free parameters of the compensation function with the properties of the material; and
   v) determining the material properties of the material by comparison of a current measurement with reference values of these parameters using the free parameters of the compensation function.

2. The method according to claim 1, further comprising:
   determining automatically the arrival time of an ultrasound wave (initial use) is with an algorithm which is based on the sum of the partial energy of the digitized received signal, wherein the energy course $S$, of the digitized signal is determined by the sum of the amplitude squares $x_k^z$:

$$S_i = \sum_{k=0}^{i} x_k^2$$

wherein $x_k$ is the $k^{th}$ sample point of the digitized signal and the minimum of the energy course $S_i$ is determined which results from correction of $S_i$ with a trend $\delta$:

$$S_i' = \sum_{k=0}^{i} x_k^2 - i\delta$$

where $$\delta = \frac{S_N}{\alpha \cdot N},$$

wherein $S_N'$ is the partial energy at the last sample point N and a is iteratively determined through comparison of the corrected energy course S; with the measured wave shape of a received ultrasound signal, and the arrival time of the ultrasound wave (initial use) is associated with the minimum of the corrected energy course $S_i$.

3. The method according to claim 1 wherein the compensating function is the Boltzmann function.

4. The method according to claim 3, further comprising:
   determining automatically the arrival time of an ultrasound wave (initial use) is with an algorithm which is based on the sum of the partial energy of the digitized received signal, wherein the energy course S, of the digitized signal is determined by the sum of the amplitude squares $x_k^z$:

$$S_i = \sum_{k=0}^{i} x_k^2$$

wherein $x_k$ is the $k^{th}$ sample point of the digitized signal and the minimum of the energy course $S_i'$ is determined which results from correction of $S_i$ with a trend $\delta$:

$$S_i' = \sum_{k=0}^{i} x_k^2 - i\delta$$

where $$\delta = \frac{S_N}{\alpha \cdot N},$$

wherein $S_N$ is the partial energy at the last sample point N and a is iteratively determined through comparison of the corrected energy course S; with the measured wave shape of a received ultrasound signal, and the arrival time of the ultrasound wave (initial use) is associated with the minimum of the corrected energy course $S_i$.

* * * * *